United States Patent
MacDonald

(10) Patent No.: US 9,399,589 B2
(45) Date of Patent: Jul. 26, 2016

(54) SYNTHETIC BASE AND ASSOCIATED METHODS

(71) Applicant: Green Products & Technologies, L.L.C., Melbourne, FL (US)

(72) Inventor: John T. MacDonald, Grant, FL (US)

(73) Assignee: Green Products & Technologies, L.L.C, Melbourne, FL (US)

( * ) Notice: Subject to any disclaimer, the term of this patent is extended or adjusted under 35 U.S.C. 154(b) by 0 days.

(21) Appl. No.: 14/585,774

(22) Filed: Dec. 30, 2014

(65) Prior Publication Data

US 2015/0183669 A1 Jul. 2, 2015

Related U.S. Application Data

(60) Provisional application No. 61/921,813, filed on Dec. 30, 2013.

(51) Int. Cl.

| | |
|---|---|
| *C02F 1/66* | (2006.01) |
| *C01F 11/02* | (2006.01) |
| *C09K 8/62* | (2006.01) |
| *D21H 17/00* | (2006.01) |
| *C09K 8/38* | (2006.01) |
| *D21H 17/66* | (2006.01) |
| *D21H 17/67* | (2006.01) |
| *D21H 17/14* | (2006.01) |
| *C08J 11/28* | (2006.01) |
| *E21B 43/24* | (2006.01) |
| *C02F 103/12* | (2006.01) |

(52) U.S. Cl.
CPC . *C02F 1/66* (2013.01); *C01F 11/02* (2013.01); *C08J 11/28* (2013.01); *C09K 8/38* (2013.01); *C09K 8/62* (2013.01); *D21H 17/14* (2013.01); *D21H 17/66* (2013.01); *D21H 17/675* (2013.01); *D21H 17/74* (2013.01); *E21B 43/2406* (2013.01); *C02F 2103/12* (2013.01)

(58) Field of Classification Search
CPC .......................................................... C02F 1/66
USPC .......................................................... 514/769
See application file for complete search history.

(56) References Cited

U.S. PATENT DOCUMENTS

| | | | |
|---|---|---|---|
| 4,830,716 A | 5/1989 | Ashmead | |
| 5,229,488 A | 7/1993 | Nagasuna et al. | |
| 2008/0058229 A1 | 3/2008 | Berkland et al. | |
| 2011/0048660 A1 | 3/2011 | Esser et al. | |

FOREIGN PATENT DOCUMENTS

| | | |
|---|---|---|
| WO | 9622352 | 7/1996 |
| WO | 2012148397 A1 | 11/2012 |

OTHER PUBLICATIONS

MDOT Storm Water Management Team and Its Consultant, Tetra Tech MDOT's Storm Water Managment Program—Pollution Prevention and Good Housekeeping on Construction Sites; 1-3, 2006 (retrieved from the Internet); Retrieved on Mar. 9, 2015;URL: http://michigan.gov/documents/stormwatermgt/MDOT_MS4_Pollution_on_Construction_Sites_208461_7.PDF, Sep. 2006.
International Search Report of PCT/US2014/072701, published Jul. 9, 2015.

*Primary Examiner* — Taofiq A Solola
(74) *Attorney, Agent, or Firm* — Stephen A. Anderson; GrayRobinson, P.A.

(57) ABSTRACT

Glycine is an organic compound that can be used in the making of a synthetic base that obviates all the drawbacks of strong bases such as sodium hydroxide. The new compound is made by dissolving glycine in water and adding calcium hydroxide at a molar ration of about 1:1. Next, sodium percarbonate is dissolved in the solution to produce the new compound, which can be referred to as glycine hydroxide.

11 Claims, No Drawings

SYNTHETIC BASE AND ASSOCIATED METHODS

CROSS-REFERENCE TO RELATED APPLICATION

This application claims priority to provisional application Ser. No. 61/921,813, filed Dec. 30, 2013, the contents of which are fully incorporated by reference for all purposes.

FIELD OF THE INVENTION

The present invention relates to compositions comprising synthetic bases and to methods of use for such compositions, including, but not limited to, the hydraulic fracturing of oil and gas wells, adjusting the pH of well drilling fluids during oil and gas exploration and mining, and adjusting the pH of process and waste waters.

BACKGROUND OF THE INVENTION

Bases by their very nature can be dangerous to use, handle, transport, and store. Further, most bases are hazardous to the environment.

Sodium hydroxide, for example, is a highly corrosive, strong base that is used in many industrial and household applications including surface cleaning and descaling operations, peeling aid operations, oil and gas well mud and water treatments, pH adjustments, municipal water treatments, and in the food industry. Concentrated sodium hydroxide is corrosive and dangerous to living tissue.

Thus, there is a need for a synthetic base that is less corrosive, more environmentally friendly, and safer to use for a plurality of applications.

SUMMARY OF THE INVENTION

The present invention is directed to a synthetic base, method of making, and method of using said base. The synthetic base comprises a glycine compound known as glycine hydroxide that is made by mixing glycine with calcium hydroxide and sodium percarbonate.

The application provides a method of making a synthetic base comprising mixing glycine with calcium hydroxide. In another embodiment, the method comprises mixing glycine with calcium hydroxide at a molar ratio of approximately 1:1 to produce a solution/ In yet another embodiment, the method further comprises dissolving sodium percarbonate into the solution.

The synthetic base can be used in place of a plurality of known bases, oxidizers, and disinfectants, such as, but not limited to, sodium hydroxide, potassium hydroxide, magnesium hydroxide, as well as lithium hydroxide.

Particular uses of the compositions described herein include but are not limited to use in the manufacturing of cleaning compounds, fruit and vegetable peeling aid operations, oil and gas well mud and water treatments, pH adjustments for water treatment, water based mud systems to yield gels and polymers, replacement of conventional usage of sodium hydroxide in the bitumen extraction process, regeneration of resin systems used in the process of steam assisted gravity drainage (SAGD), hydration of organic slurries relating to mud systems used in the hydraulic fracturing of rock, pH buffering for frac fluid systems, direct replacement for caustic in a cross-linked frac fluid system, and in food processing applications.

The embodiments described herein have a multiplicity of advantages and benefits, not the least of which is that the embodiments of the compositions are more environmentally friendly than typical bases, and, additionally, are deemed organic compounds. Thus, as described above, the embodiments can be used to replace traditional bases and are safer to use than existing bases.

DETAILED DESCRIPTION OF EMBODIMENTS

A description of the preferred embodiments of the invention will now be presented:

The application provides a method of making a synthetic base comprising mixing glycine with calcium hydroxide. In another embodiment, the method comprises mixing glycine with calcium hydroxide at a molar ratio of approximately 1:1 to produce a solution/ In yet another embodiment, the method further comprises dissolving sodium percarbonate into the solution.

The application also provides a method of making a synthetic base comprising:
  i) mixing glycine with calcium hydroxide with a molar ratio of approximately 1:1 to produce a solution; and
  ii) dissolving sodium percarbonate into the solution.

The application provides a method of improving hydraulic fracturing of an oil or gas well and adjusting the pH of well drilling fluids, comprising adding to at least one of the well and the drilling fluid an effective amount of a solution of glycine hydroxide in order to adjust the pH thereof to a desired level.

The application provides a method of adjusting the pH of at least one of process and waste waters, comprising adding to the at least one of the process and waste waters an effective amount of a solution of glycine hydroxide in order to adjust the pH thereof to a desired level.

The application provides a method of regenerating resin systems used in steam assisted gravity drainage, comprising adding to the resin systems an effective amount of a solution of glycine hydroxide.

The application provides a method of hydrating organic slurries, comprising adding to the organic slurries an effective amount of a solution of glycine hydroxide.

Glycine is an organic compound having the formula $NH_2CH_2COOH$. Glycine is a crystalline solid that is known to be used commercially in pharmaceutical applications, as an agent in metal chelation, as an animal food additive, and in cosmetics.

Herein described is a new use for glycine in the making of a synthetic base that substantially reduces negative environmental, industrial, and personal impacts associated with the use of strong bases such as sodium hydroxide.

One embodiment of the synthetic base disclosed herein is made by treating glycine with a 25% solution of calcium hydroxide, in a molar ratio of approximately 1:1. The mixture is allowed to react, for example, for approximately 30 minutes or until the glycine is essentially fully dissolved in the calcium hydroxide solution. In one embodiment of the invention, an inline eductor is used to decrease the time required for the glycine to dissolve in the solution.

In one embodiment, once dissolution of the glycine in the calcium hydroxide solution is complete, sodium percarbonate is then dissolved in the solution, resulting in an embodiment of the synthetic base, which will be referred to herein as glycine hydroxide.

In the embodiment outlined above, 25% by weight of sodium percarbonate is introduced into the solution and allowed to react until a complete dissolution is achieved, requiring approximately an additional 30 minutes. It is noted that the vessels used for reaction are preferably capable of withstanding extreme heat for extended periods of time as the reaction is quite exothermic, thus releasing energy from the synthesis. Thus, ideally, the product should be allowed to reach ambient temperature prior to transferring to smaller vessels or containers.

It has been discovered that, not only does the synthetic base described herein serve to replace most traditionally used bases, but embodiments of glycine hydroxide as described herein have been found to be less caustic than typical strong bases, as well as to moderate other strong bases interacting with substrates. For example, when sodium hydroxide is placed on a metal such as aluminum or steel, a dangerous and corrosive reaction takes place. However, when glycine hydroxide as described herein is added to sodium hydroxide on such a metal surface, the reaction is substantially and immediately minimized, and corrosion is essentially prevented from occurring.

Particular non-limiting uses of the embodiments disclosed herein include the manufacturing of cleaning compounds, including but not limited to carpet stain removers, cleaning compounds for cars, boats, trains, and other vehicles, household cleaners and other janitorial supplies, degreasers, upholstery cleaners, driveway cleaners, and soot removers for removing soot after a fire or other instances in which removal of soot is desirable.

Further non-limiting uses of the embodiments disclosed include use in oil and gas well mud and water treatments, pH adjustments for water treatment, including but not limited to waste water treatment plants, water based mud systems to yield gels and polymers, replacement of conventional usage of sodium hydroxide in the bitumen extraction process, regeneration of resin systems used in the process of steam assisted gravity drainage (SAGD), hydration and/or pH adjustment of organic slurries relating to mud systems used in the process of hydraulic fracturing of rock prior to recirculation into a drilling well, pH buffering of frac fluid and/or direct replacement for caustic in a cross-linked frac fluid system or systems relating to the hydraulic fracturing of rock, and in the food processing industries, including fruit and vegetable peeling aid operations, and food juicing factories.

Other uses for the embodiments disclosed herein include use in the paper manufacturing industry, including adjusting the pH level of pulp systems and cleaning fabric used during the paper manufacturing process.

Even further uses for the embodiments described herein include the cleaning and pH adjustment of concrete plant washout pits, adjusting the pH of ponds, and adjusting the pH of closed-loop fluid systems relating to factories.

General Conditions

Compounds of the invention can be made by a variety of methods depicted in the illustrative synthetic reactions described herein.

The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991, Volumes 1-15; Rodd's *Chemistry of Carbon Compounds*, Elsevier Science Publishers, 1989, Volumes 1-5 and Supplementals; and *Organic Reactions*, Wiley & Sons: New York, 1991, Volumes 1-40, the contents of which are fully incorporated by reference herein for all purposes. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

The reactions described herein are typically conducted at atmospheric pressure at a reaction temperature range of from about −78° C. to about 150° C., often from about 0° C. to about 125° C., and more often and conveniently at about room (or ambient) temperature, e.g., about 20° C. However, other temperatures and pressures are considered to be within the scope of the present disclosure.

Various substituents on the compounds of the invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "*Protective Groups in Organic Synthesis*" by Green et al., John Wiley and Sons, 1999, the contents of which are fully incorporated by reference herein for all purposes. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alternate reactions can be employed to provide a variety of substituents throughout the molecules of the starting materials, intermediates, or the final product, including isolated products.

The features disclosed in the foregoing description, or the following claims, or any structures or reactions, expressed in their specific forms or in terms of a means for performing the disclosed function, or a method or process for attaining the disclosed result, as appropriate, may, separately, or in any combination of such features, be utilized for realizing the embodiments in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A method of making a composition, the method comprising:
   mixing glycine with calcium hydroxide to produce a solution; and
   adding sodium percarbonate to the solution.

2. The method as described in claim 1, wherein the glycine and the calcium hydroxide are mixed at a molar ratio of about 1:1.

3. The method as described in claim 2, wherein the sodium percarbonate is added at a concentration of about 25% by weight of the solution.

4. A method of adjusting the pH of a fluid, the method comprising:
   adding to the fluid a composition comprising glycine, calcium hydroxide, and sodium percarbonate to adjust the pH thereof to a predetermined level.

5. The method as described in claim 4, wherein the fluid comprises an oil well drilling fluid.

6. The method as described in claim 4, wherein the fluid comprises a gas well drilling fluid.

7. The method as described in claim 4, wherein the fluid comprises a process water.

8. A method as described in claim 4, wherein the fluid comprises a waste water.

9. A method for treating a system, the method comprising adding to the system a composition comprising glycine, calcium hydroxide, and sodium percarbonate;
   wherein the system comprises at least one of a resin system, an organic slurry, a concrete plant washout pit, a waste water treatment plant, a water-based mud system for yielding at least one of a gel and a polymer, a bitumen extraction system, and a pulp system used in the manufacture of paper.

10. The method as described in claim 9, wherein the resin system comprises a resin system used in the process of steam-assisted gravity drainage.

11. A composition comprising glycine, calcium hydroxide, and sodium percarbonate.

\* \* \* \* \*